United States Patent
Hannon et al.

(10) Patent No.: US 8,364,241 B2
(45) Date of Patent: Jan. 29, 2013

(54) SYSTEM AND METHOD FOR PAIRING A WIRELESS DEVICE WITH A SYSTEM THROUGH A CHARGE CRADLE

(75) Inventors: Jeremy Patrick Hannon, Milwaukee, WI (US); Jonathan Mark Butzine, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 197 days.

(21) Appl. No.: 12/814,705

(22) Filed: Jun. 14, 2010

(65) Prior Publication Data

US 2011/0306882 A1 Dec. 15, 2011

(51) Int. Cl.
*A61B 5/05* (2006.01)
(52) U.S. Cl. ......... 600/407; 600/437; 378/114; 378/117
(58) Field of Classification Search .......... 600/407–429, 600/437–459; 378/10–118
See application file for complete search history.

(56) References Cited

U.S. PATENT DOCUMENTS

| | | | |
|---|---|---|---|
| 5,223,875 A * | 6/1993 | Yanagisawa | 396/58 |
| 6,252,358 B1 * | 6/2001 | Xydis et al. | 315/295 |
| 6,803,543 B2 | 10/2004 | Argersinger et al. | |
| 7,261,465 B2 | 8/2007 | Butzine et al. | |
| 7,283,615 B2 * | 10/2007 | Morehead | 378/117 |
| 7,298,825 B2 * | 11/2007 | Omernick et al. | 378/116 |
| 7,364,358 B1 | 4/2008 | Butzine | |
| 7,483,516 B2 * | 1/2009 | Coombs | 378/114 |
| 7,502,444 B2 * | 3/2009 | Marar | 378/98 |
| 7,682,077 B2 | 3/2010 | Halsmer et al. | |
| 2004/0206738 A1 | 10/2004 | Argersinger et al. | |
| 2006/0242268 A1 * | 10/2006 | Omernick et al. | 709/219 |
| 2007/0184847 A1 * | 8/2007 | Hansen et al. | 455/456.1 |
| 2007/0189462 A1 * | 8/2007 | Spahn | 378/193 |
| 2007/0202836 A1 | 8/2007 | Zaman et al. | |
| 2008/0069304 A1 * | 3/2008 | Muszak et al. | 378/114 |
| 2008/0130835 A1 | 6/2008 | Peterson et al. | |
| 2008/0208627 A1 * | 8/2008 | Skyggebjerg | 705/2 |
| 2008/0240343 A1 * | 10/2008 | Jabri et al. | 378/22 |
| 2009/0046463 A1 | 2/2009 | Coombs et al. | |
| 2009/0129546 A1 * | 5/2009 | Newman et al. | 378/114 |
| 2009/0224935 A1 * | 9/2009 | Kagermeier et al. | 340/825.72 |
| 2010/0104066 A1 * | 4/2010 | Foos et al. | 378/62 |
| 2011/0105904 A1 * | 5/2011 | Watanabe | 600/443 |

OTHER PUBLICATIONS

U.S. Appl. No. 12/786,323, filed May 24, 2010, Jonathan Mark Butzine.
U.S. Appl. No. 12/786,332, filed May 24, 2010, Jonathan Mark Butzine.
U.S. Appl. No. 12/786,357, filed May 24, 2010, Jonathan Mark Butzine.
U.S. Appl. No. 12/786,363, filed May 24, 2010, Jonathan Mark Butzine.
U.S. Appl. No. 12/786,371, filed May 24, 2010, Jon Charles Omernick.

* cited by examiner

*Primary Examiner* — Sanjay Cattungal
(74) *Attorney, Agent, or Firm* — Fletcher Yoder, P.C.

(57) ABSTRACT

A system and method for pairing an X-ray system with a wireless device is provided. In one embodiment, a method includes generating a unique pairing code with control circuitry that controls the operation of the X-ray system, providing the unique pairing code to the wireless device in the form of a pulse sequence and receiving a wireless signal indicative of the unique pairing code from the wireless device. The wireless device is then paired and enabled for use with the X-ray system.

35 Claims, 5 Drawing Sheets

SYSTEM AND METHOD FOR PAIRING A WIRELESS DEVICE WITH A SYSTEM THROUGH A CHARGE CRADLE

BACKGROUND OF THE INVENTION

The subject matter disclosed herein relates to pairing devices with systems via charge pulse sequences.

A number of radiological imaging systems of various designs are known and are presently in use. Such systems are based upon generation of X-rays that are directed toward a subject of interest. The X-rays traverse the subject and impact a film or a digital detector. In medical diagnostic contexts, for example, such systems may be used to visualize internal tissues and diagnose patient ailments. In other contexts, parts, baggage, parcels, and other subjects may be imaged to assess their contents and for other purposes. In general, X-ray systems of the type referred to by the present disclosure may include projection X-ray systems, fluoroscopic systems, X-ray tomosynthesis systems, computed tomography systems, and various mixed or combined-modality systems that utilize X-ray imaging in conjunction with other imaging physics, such as ultrasound, positron emission tomography, magnetic resonance imaging, and so forth.

In typical X-ray examination procedures, where possible, a user (e.g., an X-ray technician) is positioned away from the location of exposure, and often behind a shielded barrier to avoid or reduce exposure to radiation. To further reduce radiation exposure to the technician, the technician may utilize a handheld device to initiate exposure from a distance. In some implementations, each X-ray unit has a unique handheld device. That is, each X-ray unit may have a dedicated handheld device that is enabled for use only with that particular X-ray unit. However, in a situation where a handheld device is inadvertently switched with another, there may be an increased chance of accidental X-ray emission by using the wrong handheld device.

BRIEF DESCRIPTION OF THE INVENTION

In one embodiment, an X-ray system is provided that includes a source of X-ray radiation, control circuitry configured to control the source of X-ray radiation and to communicate via a wireless interface, and a power source operatively connected to the control circuitry and capable of generating a pulse sequence corresponding to a pairing code generated by the control circuitry. The system also includes charge circuitry electrically connected to the power source and capable of delivering the pulse sequence to any one of a plurality of handheld interface devices. The control circuitry is configured to receive a wireless signal corresponding to the generated pairing code from the one or the plurality of handheld interface devices to pair the one or the plurality of handheld interface devices with the control circuitry.

In another embodiment, a method of pairing an X-ray system with a wireless device is provided including detecting a pairing code generated by a controller of the X-ray system with a pulse sequence corresponding to the pairing code with the wireless device, transmitting a wireless signal corresponding to the pairing code to the controller with the device, performing a pairing of the wireless device and the controller, and enabling the wireless device for use with the X-ray system.

In a further embodiment, a method of pairing an X-ray system with a wireless device is provided including generating a unique pairing code with control circuitry that controls the operation of the X-ray system, providing the unique pairing code to the wireless device in the form of a pulse sequence supplied via charge circuitry operatively connected to a power supply controlled by the control circuitry, receiving a wireless signal corresponding to the unique pairing code from the wireless device, and enabling the wireless device for use with the X-ray system.

In another embodiment, a system is provided having a first medical device capable of wireless communication and a second medical device capable of wireless communication with the first medical device. The first medical device and the second medical device are configured to be dynamically paired.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
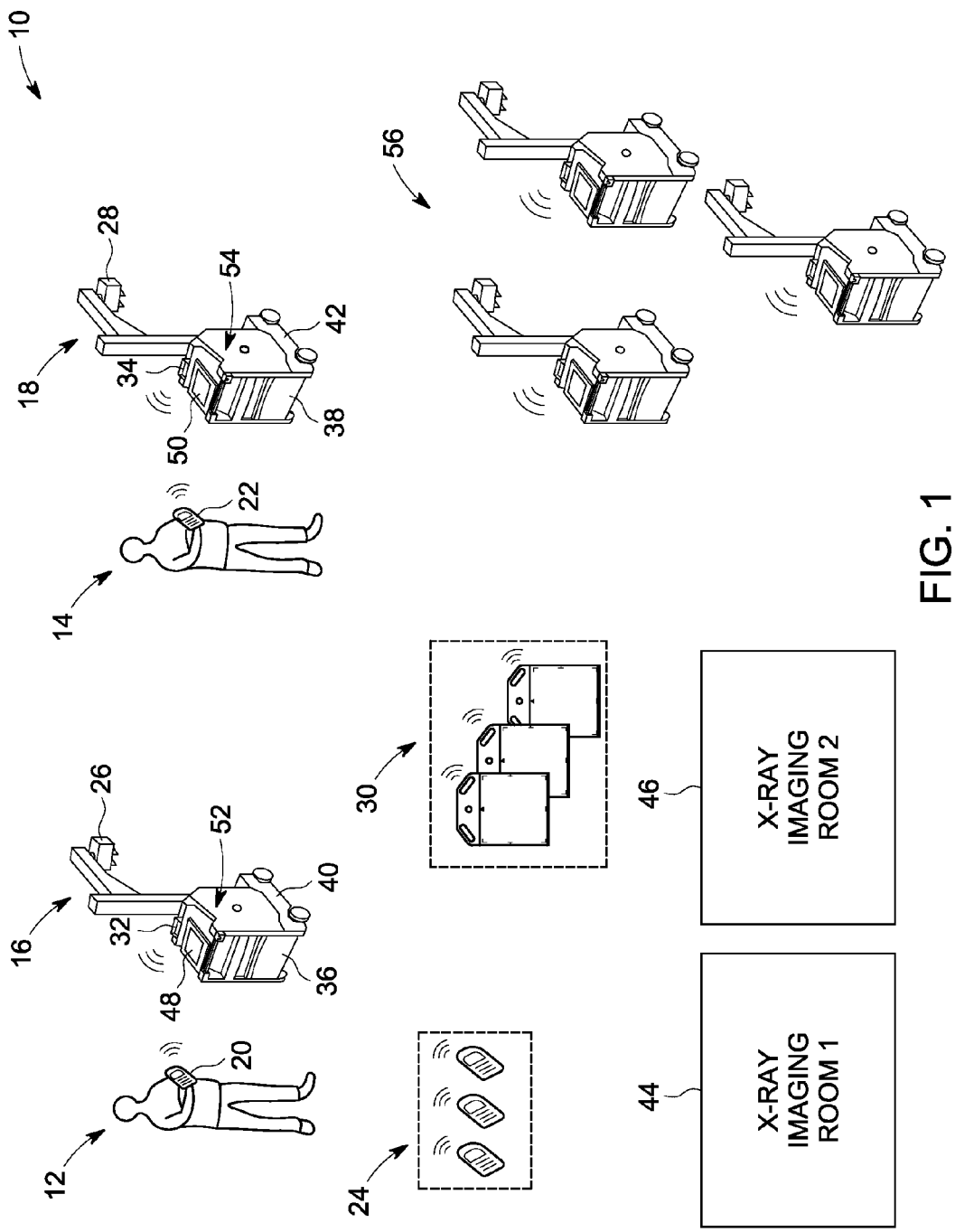
FIG. 1 is a perspective view of an embodiment of an imaging area having a plurality of handheld devices and wireless detectors and a plurality of mobile X-ray units, all of which are swappable and are able to be uniquely paired using charge sequence pairing, in accordance with present embodiments.

In situations where handheld devices (i.e., handsets) capable of controlling X-ray exposure by an X-ray unit may be inadvertently or intentionally swapped, such as by accidental droppage, changeout due to a loss of power or a technical problem with a device, or any other occurrence, it may be possible that a technician may cause inadvertent X-ray emission by using an incorrect handheld device (i.e., a handheld device connected to a different X-ray unit), or it may be impossible to operate the system at all if it is disabled by a lack of pairing with the particular device in the possession of the technician. In wireless arrangements, the X-ray unit may have difficulty recognizing incorrect handheld devices, as the devices are not directly tethered to the X-ray unit. Accordingly, it is now recognized that it may be desirable for an X-ray unit to be able to communicate and pair with a wireless device, such as a handheld device, such that the X-ray unit may pair and unpair on-the-fly to allow the swapping of several handheld devices. Indeed, in such arrangements, inadvertent X-ray emission (and resultant exposure) may be avoided. In present embodiments, such pairing may be accomplished when the handheld device is physically in contact with the X-ray unit, which may occur while the handheld device is being charged and/or stored in a charge cradle operatively connected to the X-ray unit.

In the present context, dynamic pairing of a wireless interface device with the system may include paring via connective and/or non-connective charging, such as direct electrical contact charging, magnetic-based (e.g., inductive) charging, capacitive charging, and so forth. Unlike other possible approaches which would require the addition of extra hardware (e.g., additional wires, optoisolators, and so on) to allow the charge cradle and the X-ray unit to directly communicate (via bidirectional communication) over dedicated wires, the present embodiments allow for a reduction in cabling, only requiring power to the device being charged and wireless capability. Additionally, some handheld devices may be space-constrained, and adding two more communication pins would require the connector to have 4 or 5 pins rather than simply a power cord. However, the present embodiments may be applied to existing systems (such as via a software update), or may be applied by retrofitting. Technical advantages of the disclosed embodiments may therefore include a reduction in space and/or wiring, no complicated button sequences or user interaction required to complete pairing, as well as an increase in workflow capability. For example, wireless devices, such as handheld devices and/or wireless detectors, may be swappable and pairable (i.e., may be dynamically paired) with a variety of X-ray units simply by placing them in respective charge cradles of an X-ray unit that a technician intends to utilize for imaging. Therefore, greater time for imaging and patient care may be afforded, rather than a reduction in efficiency due to mismatched devices.

In a general sense, wireless devices may be paired with respective X-ray units by placing the wireless device in a charge cradle. The wireless device, upon detecting that it is in the charge cradle (or more generally, that it is being charged), wirelessly sends a request for a pairing code to the X-ray unit (e.g., a system controller). The X-ray unit detects the wireless request, and generates a random number (e.g., an 8 bit number). The X-ray unit cycles power to the wireless device with a charge pulse sequence representative of the random number via the charge cradle. The wireless device determines the random number by detecting the on/off states of the power to the charge cradle, and wirelessly communicates back to the X-ray unit the random number that it received. After confirming that the wireless device has communicated the correct number, the wireless device is then enabled for use with the X-ray unit. Therefore, the communication loop for pairing may be as follows: from the X-ray unit (e.g., a system controller and power supply) to the charge cradle (or charge cable) via an electrical connection, to the wireless device from the charge cradle via a charge sequence (i.e., another electrical connection), and back to the X-ray unit from the wireless device via wireless communication. Therefore, the present approaches to dynamic pairing may be implemented using existing hardware that is already present on the paired devices.

The advantages of the present embodiments may be appreciated with reference to FIG. 1, which is a view of an imaging area 10. For example, at the beginning of a shift or work day, a first user 12 and second user 14 may be assigned to or pick out respective first mobile X-ray unit 16 and second mobile X-ray unit 18. It should be noted that while the present embodiments are discussed in the context of mobile X-ray units, that they are equally applicable to a variety of imaging arrangements, such as dedicated X-ray imaging rooms or areas with stationary or movement-constrained equipment, as well as non-X-ray mobile systems (e.g., mobile ultrasound systems) with wireless control devices. The present embodiments are also applicable to imaging modalities such as CT, MRI, PET, and so forth. Therefore, the wireless communication and dynamic pairing described herein may be applicable to a patient table, a mobility control unit, an imaging control unit, a detector unit, and so on. Nevertheless, to allow the first and second users 12, 14 to perform patient imaging, such as from a distance, a respective first handheld device 20 and a second handheld device 22 may also be assigned to each user, with each handheld device being selected from a plurality of handheld devices 24. The handheld devices may have simple configurations, such as handswitches that switch between, for example, an off and on state of an X-ray source, or may have more complex configurations, such as personal data assistants (PDA's) that enable a user to view and manipulate various operational parameters, and so on. In the present context, the first handheld device 20 may operate the first mobile X-ray unit 16 and the second handheld device 22 may operate the second mobile X-ray unit 18, as discussed herein, such as to drive each unit, control exposure to each unit, and so on. In some embodiments, in addition to other possible features discussed below, each handheld device 20, 22 may initiate exposure by a first X-ray source 26 and a second X-ray source 28 of their respective X-ray units, such as by pressing an exposure button on each device.

The X-ray imaging may be performed by X-ray emission using X-ray sources 26, 28 and one or more wireless X-ray detectors. While performing X-ray imaging, each user may utilize one or more of the X-ray wireless detectors 30 to detect the emitted (and attenuated) X-rays generated by the X-ray sources 26, 28 upon exposure initiation by the handheld devices 20, 22. Conversely, when imaging is not performed, such as before an imaging sequence or as the mobile X-ray units 16, 18 are being moved from one area to another, the first user 12 may place the first handheld device 20 in a first charge cradle 32 of the first mobile X-ray unit 16, for example to store or charge the first handheld device 20. In some configurations, the first charge cradle 32 may have a switch that, when activated (such as by placing the first handheld device 20 in the cradle 32), completes a circuit and allows charge to flow from the charge cradle 32 and to the handheld device 20. Again, as noted above, the electrical connection may be a contact connection or, alternatively, a non-contact connection such as an inductive or capacitive connection. In other arrangements, charge may substantially continuously be present in the charge cradle 32, such that no switch is present. Further, while the present discussion is directed towards charging the handheld device 20 and/or the wireless X-ray detector 30 in a charge cradle, it should also be noted that other devices capable of providing a charge are also contemplated herein, such as a docking station or a simple cord capable of conditioning and providing power in cycles. According to present embodiments, placing the first handheld device 20 in the first charge cradle 32 also initiates a pairing sequence between the first handheld device 20 and the first mobile X-ray unit 16. The pairing sequence, in some arrangements, gives the first user 12 the ability to control emission by the first X-ray source 26 using the first handheld device 20. Additionally, in some embodiments, such as when the wireless handheld device 20 has a screen or similar user interface, the pairing may allow the first user 12 to view operational parameters of the first mobile X-ray unit 16, view images generated from imaging procedures, and so forth. In a similar manner, the second user 14 may initiate a pairing sequence upon placing the second handheld device 22 in a second charge cradle 34. In this way, the second handheld device 22 is paired to the second mobile X-ray unit 18, and the second user 14 is able to initiate X-ray emission using the second handheld device 22.

Additionally or alternatively, the wireless X-ray detectors 30 may be stored, charged, and/or paired with each mobile X-ray unit 16, 18 in a similar manner to that described for the handheld devices 20, 22. That is, the first user 12 may place one or more of the wireless X-ray detectors 30 into a first detector charge slot 36 (i.e., a detector charge cradle) for storage and charging within the first mobile X-ray unit 16. Indeed, by placing one or more wireless X-ray detectors 30 into the first detector charge slot 36, a pairing sequence may be initiated to enable use with the first X-ray mobile unit 16. Specifically, the pairing may allow the one or more wireless X-ray detectors 30 to communicate with and provide image data wirelessly to the first mobile X-ray unit 16. In some embodiments, pairing one or more wireless X-ray detectors 30 with the first mobile X-ray unit 16 may enable X-ray emission by the first X-ray source 26. Similarly, the second user 14 may place one or more wireless detectors 30 into a second detector charge slot 38, such that the detectors placed therein are enabled for use with the second mobile X-ray unit 18.

As noted above, the charge cradles 32, 34, 36, and 38 of the first and second mobile X-ray units 16, 18 allow the handheld devices 20 and 22 as well as the wireless X-ray detectors 30 to be stored and charged while the mobile X-ray units 16 and 18 are not in use. For example, when the first and second mobile X-ray units 16 and 18 are being transported, for example to an imaging area, the charge cradles 32, 34, 36, and 38 may charge their respective wireless devices and ensure that the devices are properly paired with the appropriate mobile X-ray unit. Further, the mobile X-ray units 16 and 18 may have wheeled bases 40 and 42 that allow the first and second users 12 and 14 to move each unit to an appropriate imaging area, for example a patient bed or a stationary examination room, such as a first X-ray imaging room 44 or a second X-ray imaging room 46. In some embodiments, the paired wireless devices 20 and 22 may control the driving of their respective mobile units.

In some circumstances, the first X-ray mobile unit 16 and the second mobile X-ray unit 18 may be deployed in close proximity, such as when the first X-ray imaging room 44 and the second X-ray imaging room 46 are next to each other. Indeed, the first user 12 with the first handheld device 20 may be within wireless range of the second mobile X-ray unit 18, and the second user 14 with the second handheld device 22 may be within wireless range of the first mobile X-ray unit 16. In accordance with the embodiments described herein, the pairing processes that result from the act of placing the first handheld device 20 into the first charge cradle 32 and the second handheld device 22 into the second charge cradle 34 may prevent the first user 12 from inadvertently initiating an exposure by the second mobile X-ray unit 18 and the second user 14 from inadvertently initiating an exposure by the first mobile X-ray unit 16. Further, should situations arise in which the first and second users 12 and 14 exchange mobile X-ray units, the first user 12 may utilize the first handheld device 20 to control the second mobile X-ray unit 18 simply by placing the first handheld device 20 into the second charge cradle 34, and the second user 14 may utilize the second handheld device 22 to control the first mobile X-ray unit 16 simply by placing the second handheld device 22 into the first charge cradle 32. Accordingly, it should be noted that when a handheld device (e.g., one of the plurality of handheld devices 24) is placed into a charge cradle to which the handheld device is not paired, that the mobile X-ray unit 16, 18 may unpair all previously paired devices of similar type. Therefore, the pairing process initiated by the charge cradles 32, 34, 36, and 38 render the wireless devices 20, 22, 24, and 30 fully swappable, such that seamless control of each imaging unit may be possible. Further, it should be noted that in some of the disclosed embodiments, the act of pairing or unpairing a wireless device with a system may result in wireless notifications of such pairing and/or unpairing being provided to other systems and wireless devices.

The first and second mobile X-ray units 16 and 18 may also include a first and second display 48 and 50, respectively, which allow each user 12 and 14 to view paired devices, operational parameters, image data, images, and so forth. The displays 48 and 50 may be touchscreens or may be, in conjunction with other user inputs, connected to control circuitry 52 within the first mobile X-ray unit 16 and control circuitry 54 within the second mobile X-ray unit 18, respectively. The control circuitry 52 and 54 allow the users 12 and 14 to add or change acquisition parameters, to identify paired devices, to manipulate patient and/or image data, and so on. In addition to allowing the users 12 and 14 to perform the acts above, the control circuitry 52 and 54 may also provide the mobile X-ray units 16 and 18 with the functional hardware capable of performing the pairing sequences.

For example, in a pairing sequence according to present embodiments, after the first handheld device 20 is placed in the first charge cradle 32, the first handheld device 20 may recognize that it is in the cradle 32 (e.g., via an applied charge), and send a wireless signal to the control circuitry 52 within the first mobile X-ray unit 16. The wireless signal may be an initiation signal (i.e., an invitation) for the control circuitry 52 to generate a random or unique code. The unique code is then provided to the first handheld device 20 as a series of on/off charge pulse sequences via the charge cradle 32. The first handheld device 20 then wirelessly transmits a signal indicative of or corresponding to the unique code back to the control circuitry 52. Upon recognition that the wireless signal sent by the first handheld device 20 matches the unique code generated by the control circuitry 52, the control circuitry 52 then pairs the first handheld device 20 with the first mobile X-ray unit 16. As noted above, the pairing may enable certain features such as the initiation of X-ray emission, control of system motion, the ability to view and manipulate operational parameters, and so on. Further, it should be noted that the process for pairing the wireless X-ray detectors 30 with the mobile X-ray units 16 and 18 may be substantially the same with respect to the control circuitry 52 and 54 and the detector charge slots 36 and 38. Indeed, any of the plurality of handheld devices 24 and/or the plurality of wireless X-ray detectors 30 may be paired and used with any one of a plurality of mobile X-ray units 56, enabling streamlined workflow capabilities, reducing the possibility of inadvertent radiation exposure, preventing unintended motion, and preventing wasted exposures due to incorrect association of detectors.

Figure 2:
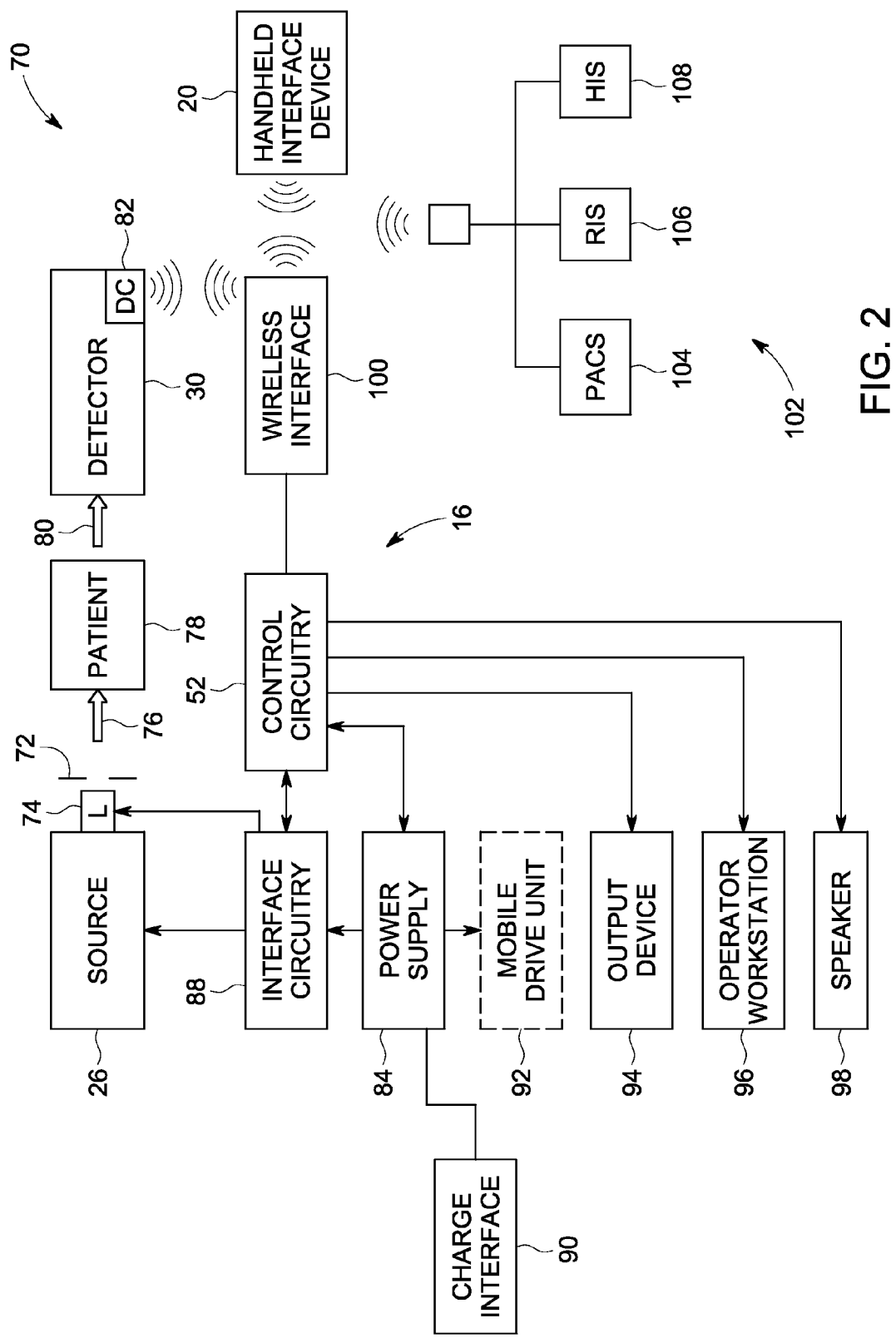
FIG. 2 is a diagrammatic illustration of an embodiment of an X-ray imager in wireless communication with a handheld interface device and a wireless X-ray detector, each of which have been paired via charge sequence pairing, in accordance with present embodiments.

The control circuitry 52 and other features for X-ray imaging are depicted in FIG. 2, which illustrates diagrammatically an X-ray system 70, such as the mobile X-ray units 16 and 18 described in FIG. 1. Indeed, the embodiments described herein may apply to many types and modalities of X-ray imaging, including both digital X-ray systems and analog X-ray systems. The X-ray system 70 includes the source of X-ray radiation 26 positioned adjacent to a collimator 72. A light source 74, also known as a collimator light, is positioned between the X-ray source 26 and the collimator 72. The collimator 72 controls the shape and extent of a stream of radiation 76 (or light), which passes into an area or a specific region of interest of a subject, such as a patient 78. The collimator light 74 directs light onto the same area where the X-ray photons will pass and can be used to position the patient 78 before exposure, which is initiated by the paired handheld device 20. A portion 80 of the radiation passes through or around the patient 78 and impacts the wireless X-ray detector 30, which is paired with the control circuitry 52. In some embodiments, the detector 30 converts the X-ray photons received on its surface to lower energy photons, and subsequently to electric signals, which are acquired and processed to reconstruct an image of the features within the patient 78.

The detector 30 is coupled to a detector controller 82 that commands acquisition of the signals generated in the detector 30. The detector controller 82 may also execute various signal processing and filtration functions, such as for initial adjustment of dynamic ranges, interleaving of digital image data, and so forth. Indeed, the detector controller 82 may facilitate pairing of the detector 30 with the control circuitry 52, as discussed below.

In general, the control circuitry 52 commands operation of the X-ray system 70 to execute examination protocols and to process acquired image data. The control circuitry 52 also includes signal processing circuitry, typically based upon a programmed general purpose or application-specific digital computer; and associated devices, such as optical memory devices, magnetic memory devices, or solid-state memory devices, for storing programs and routines executed by a processor of the computer to carry out various functionalities, as well as for storing configuration parameters and image data; interface circuits; and so forth. In the present context, as mentioned above, the control circuitry 52 is also responsible for pairing wireless devices, such as the detector 30 and the handheld interface device 20, with the X-ray system 70.

Indeed, the radiation source 26 is also controlled by the control circuitry 52, which controls signals for examination sequences. For example, the control circuitry 52 can inhibit the operation of the radiation source 26 if the correct examination conditions are not in place, such as an absence of a paired wireless X-ray detector 30. In addition, the control circuitry 52 controls a power supply 84 which supplies power to the radiation source 26, light source 74, the control circuitry 52, and interface circuitry 88. The interface circuitry 88 facilitates the provision of power to the radiation source 26, light source 74, and control circuitry 52. In addition to providing power to such functionalities, the power supply 84 also provides power to one or more charge interfaces 90, which can include the charge cradles 32, 34, 36, and/or 38 of FIG. 1. The power supply 84 also provides power to a mobile drive unit 92 (in mobile X-ray systems), for example to drive the movement of the wheeled base 40 of the first mobile X-ray unit 16.

As noted above, the control circuitry 52 is linked to at least one output device 94, such as the display 48 of FIG. 1 or a printer. The output device may include standard or special purpose computer monitors and associated processing circuitry. One or more operator workstations 96 may be further linked in the system 70 for outputting system parameters, requesting examinations, viewing images, and so forth. In general, displays, printers, workstations, and similar devices supplied within the system 70 may be local to the data acquisition components, or may be remote from these components, such as elsewhere within an institution or hospital, or in an entirely other location, linked to the image acquisition system via one or more configurable networks, such as the Internet, virtual private networks, and so forth. The control circuitry 52 may also be linked to the speaker 98 that is able to provide audible signals such as locator signals, patient-audible commands, or confirmation signals (e.g., a pairing confirmation signal).

The control circuitry 52 wirelessly communicates with the handheld interface device 20 and the wireless X-ray detector 30 via a wireless interface 100. That is, circuitry within the devices (such as the detector controller 82) is responsive to signals from control circuitry 52 communicated wirelessly via a wireless interface 100. The wireless interface 100 also enables the control circuitry 52 to receive signals, such as acquisition commands, image data, and so forth. It should be noted that the wireless interface 100 may be any type of wireless interface that allows communication via a suitable wireless communication protocol, such as an IEEE 802.15.4 standard, ultra wideband (UWB) communication standard, a Bluetooth communication standard, or any IEEE 802.11 communication standard.

The control circuitry 52 may, in some embodiments, provide the handheld interface device 20 with system operational data (e.g., inhibit of operation of radiation source), images reconstructed from image data from the detector 30, and patient data, as well as other information. The handheld interface device 20, likewise, wirelessly communicates a signal to prepare for and initiate an exposure and other commands for operation of the X-ray system 70. The handheld interface device 20, in some embodiments, may also transmit its location relative to the system 70. Additionally, the handheld interface device 20 may transmit or receive patient data and/or instructions (e.g., imaging sequences to be performed) to or from a medical facility's network 102. The medical facility network 102 includes a picture and archiving system (PACS) 104, a radiology information system (RIS) 106, and/or a hospital information system (HIS) 108 to receive or provide the information and/or instructions. In some embodiments, the handheld interface device 20 may communicate with the network 102 via the system 70 and/or the network 102 may communicate with the handheld interface device 20 via the system 70. For instance, the handheld wireless device 20 could instruct the X-ray system 70 to send a digital image directly to a remote storage or server location, such as the hospital PACS, RIS, and/or HIS system.

Figure 3:
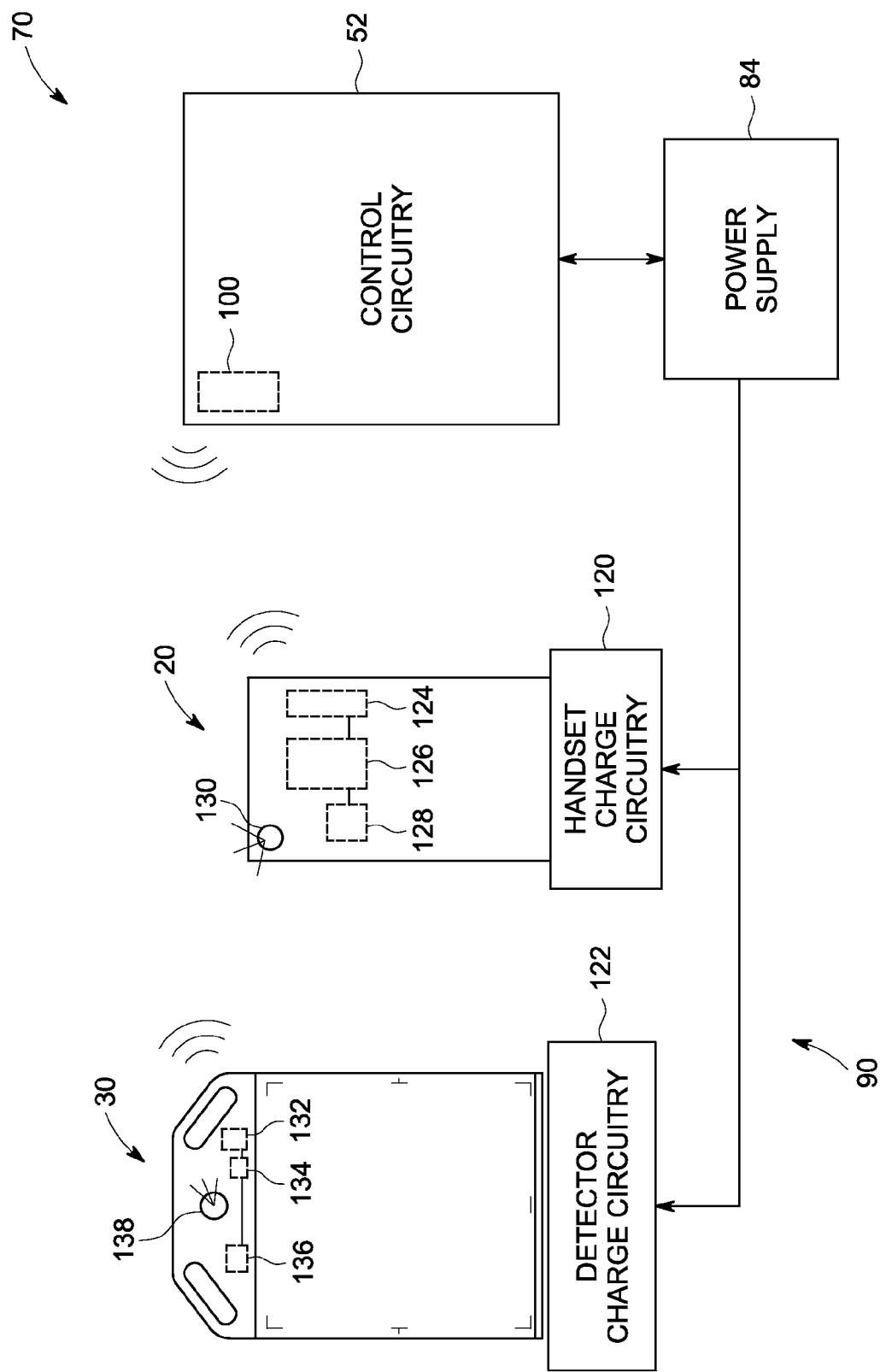
FIG. 3 is a schematic illustration of an embodiment of the handheld interface device and wireless X-ray detector in their respective charge cradles, and the charge cradles are electrically connected to the power supply that generates a charge pulse sequence from a unique code generated by the system controller of FIG. 2.

As noted above, to enable such communication and control features, the handheld device 20 and the wireless X-ray detector 30 are paired to the system 70 via control circuitry 52. Indeed, the configuration during the pairing process may form a communication loop, which is diagrammatically illustrated in FIG. 3. In FIG. 3, a portion of the system 70 is depicted where the handheld interface device 20 and the wireless X-ray detector 30 are charging via handset charge circuitry 120 and detector charge circuitry 122. Additionally, it should be noted that in some embodiments the charge circuitry 120, 122 may be a portion of the interface circuitry 90.

The handheld interface device 20 is illustrated as providing a wireless signal, such as via a wireless communication interface 124. In present embodiments, the wireless communication interface 124 allows the handheld interface device 20 to send a signal corresponding to the code generated by the control circuitry 52. For example, to pair the handheld interface device 20, the device 20 is connected to the handset charge circuitry 120, as shown. The handheld device 20 then sends a wireless signal to the control circuitry 52 that invites the control circuitry 52 to generate a unique code for pairing (e.g., an 8-bit, 16-bit, or 32-bit code based on a random or system-specific number, such as a processor clock). It should be noted that a code with a higher bit count (such as 16-bit instead of 8-bit) reduces the risk of two systems generating identical codes, increasing the guarantee of uniqueness, but a larger code may be undesirable due to the slow rise times and fall times of power supply outputs, increasing the transfer time for the code. That is, higher bit numbers may increase the pairing time. Therefore, larger-sized numbers (e.g., 16-bit, 32-bit or more) may be leveraged with appropriate pairing timeframes. Upon generating the code, the control circuitry 52 sends the code to the power supply 84. The power supply 84, which provides power to the handset charge circuitry 120, sends the code to the handset charge circuitry 120 in the form of a series of on/off charge pulses, which are then transferred to the handheld interface device 20. The handheld interface device 20 then, via a processor 126, interprets the series of on/off charge pulses as a code. The processor 126, for example using algorithms stored on memory circuitry 128, then generates a signal corresponding to the code. Indeed, the memory circuitry 128 may store other information such as exposure sequences, image data, and so forth, depending on the capabilities of the handheld device 20. The signal is then sent via the wireless interface 124 back to the control circuitry 52. Once the control circuitry 52 determines that the signal sent by the handheld interface device 20 is the same as the unique code, the control circuitry 52 may then allow for the handheld device 20 to be enabled for use with the system 70.

The handheld interface device 20, in some embodiments, may provide a user-perceivable indication of pairing. In the illustrated embodiment, the handheld device 20 has a visual indicator 130, such as an LED or a light that indicates the status of the handheld interface device 20. However, it should be noted that in other embodiments the indicator may be auditory (e.g., a series of beeps or trills) or tactile (e.g., vibration or vibration pulses), or any combination of these. The light 130 may blink or change color or hue when the pairing status of the handheld device 20 changes. As an example, the light 130 may be one color when the handheld interface device is unpaired (e.g., red), a second color during the pairing process (e.g., yellow), and a third color after the pairing process is complete (e.g., green). Such indications are described in U.S. patent application Ser. No. 12/776,166, filed on May 7, 2010, which is hereby incorporated by reference.

In embodiments where the wireless X-ray detector 30 is able to be paired with the system 70, the wireless X-ray detector 30 may initiate the pairing sequence in addition to or in lieu of the handheld interface device 20 by sending an invitation signal via wireless interface 132. Thereafter, in a similar manner to that described above with respect to the handheld interface device 20, the power supply 84 may provide the unique code to the detector charge circuitry 122 in the form of an on/off charge pulse sequence. Accordingly, the detector charge circuitry 122 provides the on/off charge pulse sequence to the wireless X-ray detector 30. A processor 134 within the detector 30 (e.g., the detector controller 82) may interpret the sequence as a code and, using one or more algorithms stored on memory circuitry 136, generate a signal corresponding to the code. The signal may then be sent wirelessly back to the control circuitry 52 which, upon confirming the correctness of the signal, may then allow for the wireless X-ray detector 30 to be enabled for use with the system 70. The routine for automatic configuration of the wireless X-ray detector 30 for use with the system 70 may occur as previously described in U.S. patent application Ser. No. 11/164,438, filed Nov. 22, 2005, which is hereby incorporated by reference. Indeed, in a manner similar to the handheld interface device 20, the wireless X-ray detector 30 may include a visual indication 138 or other user-perceivable indication of the pairing state of the wireless X-ray detector 30.

Figure 4:
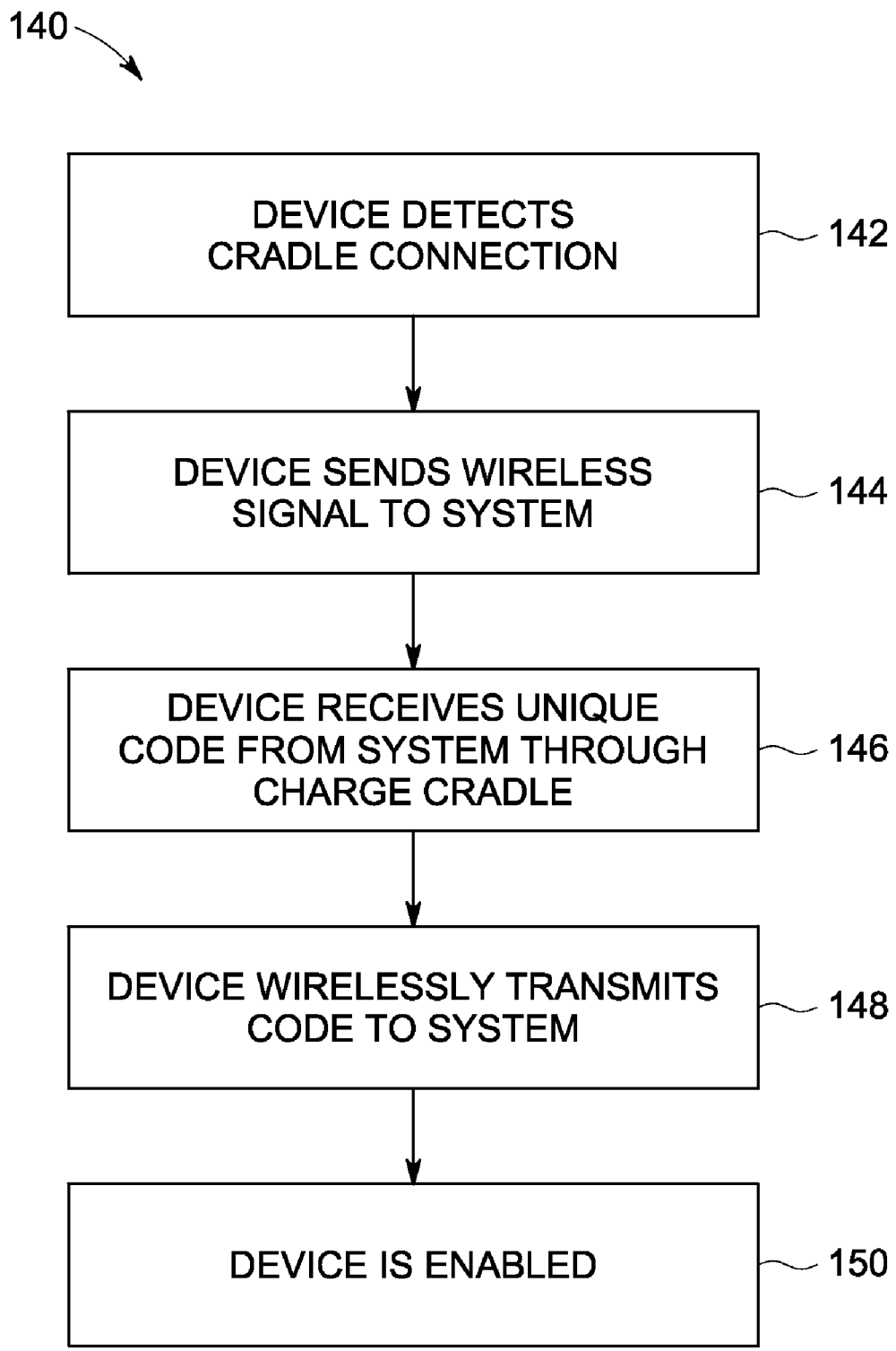
FIG. 4 is a process-flow diagram illustrating an embodiment of a method of pairing a wireless device with an X-ray system from the perspective of the wireless device, in accordance with present embodiments.

In addition to the systems described above with respect to FIGS. 1-3, the present embodiments also provide a method for pairing a wireless device with a system via a charge cradle. Specifically, FIG. 4 is a process flow diagram of a method of performing such pairing from the perspective of the wireless device. In performing the pairing, it should be noted that the pairing process may be at least partially or entirely initiated by a user, who must place the wireless device in the charge cradle to initiate pairing.

Therefore, after the user has placed the wireless device (e.g., the handheld interface device 20 and/or the wireless X-ray device 30 described above) into the charge cradle (e.g., charge cradle 32), the device detects connection with the cradle (block 142). For example, the device may detect that charge is being provided, or the cradle may initiate a unique mechanical switch that allows the wireless device to detect the connection. The wireless device then sends a wireless signal to the system (e.g., the X-ray system 70) (block 144) via a wireless interface, the signal being an invitation to generate a unique pairing code.

Through the charge cradle to which the wireless device is electrically coupled, the device may then receive the unique code in the form of a charge sequence (block 146). In present embodiments, the charge sequence may be a series of on and off states, which correspond to a pulse sequence indicative of the code. However, it should be noted that other charge sequences are also contemplated herein, such as low voltage/high voltage sequences, low power/high power sequences, low current/high current sequences, and so on. After receiving the charge pulse sequence, the device may then wirelessly transmit a signal indicative of the unique code back to the system (block 148). In embodiments where the signal matches the unique code, the device is enabled for use with the system (block 150).

Figure 5:
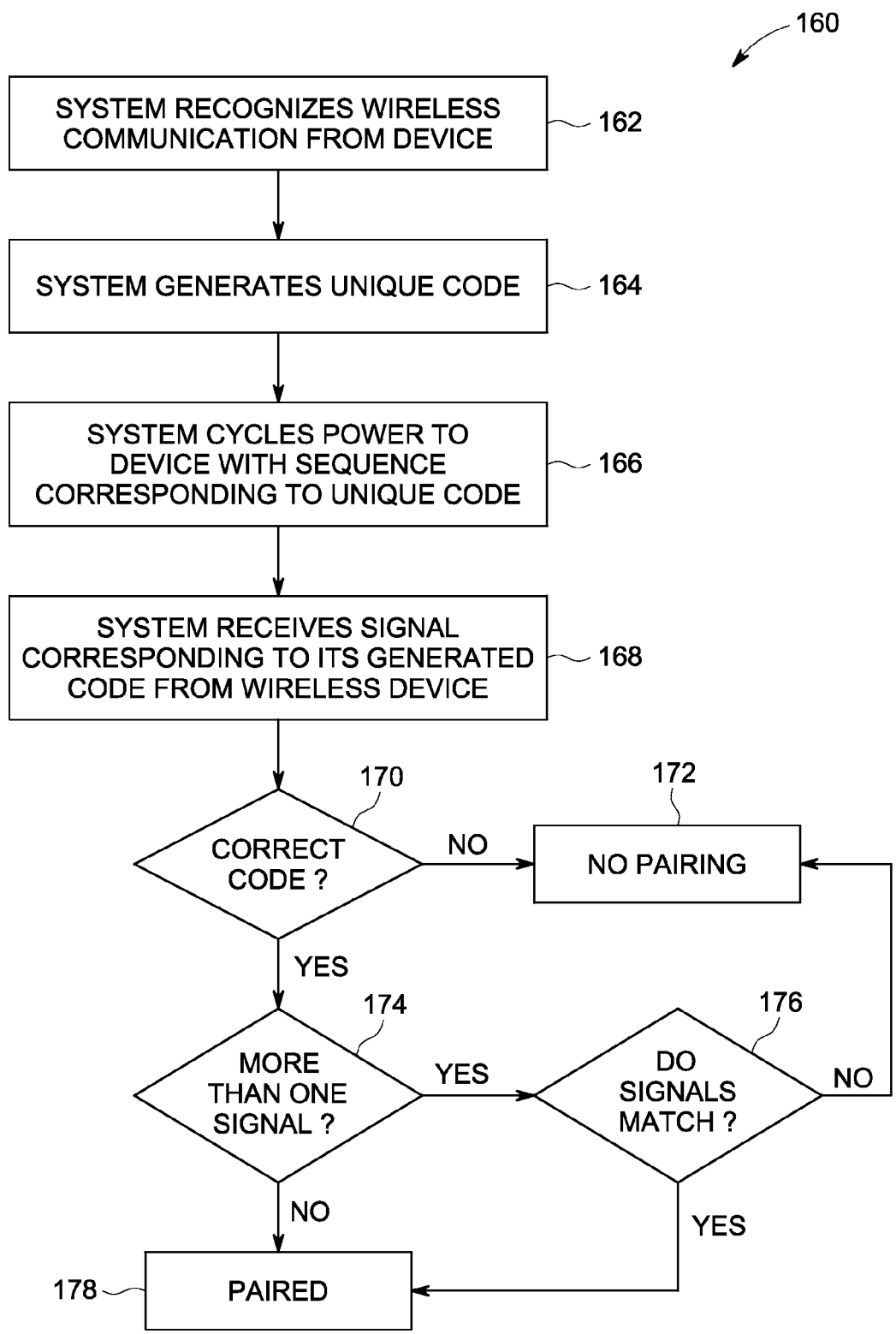
FIG. 5 is a process-flow diagram illustrating another embodiment of a method of pairing a wireless device with an X-ray system from the perspective of the X-ray system, in accordance with present embodiments.

FIG. 5 is a process flow diagram illustrating a method 160 performed by the system (e.g., system 70), for example, in conjunction with the method 140 performed by the device. The method 160 begins after the device (or plurality of devices) has been placed in its respective charge cradle and sends the invitation signal, as described above. The system receives the wireless invitation signal, and recognizes that a wireless device is attempting to be paired (block 162). The system may then generate a unique code (block 164) which may be random or may be based upon system-specific data such as a processor clock, the wireless hardware MAC address, an identification tag, a service tag, analog sensor input, or similar feature. Further, the code may be 8-bit, 16-bit, or any plurality of bits, as discussed above.

Upon generating the code (block 164), the system then cycles power to the device with a charge pulse sequence corresponding to the generated code (block 166). For example, control circuitry or similar processing circuitry of the system may generate the code and provide the code to a power supply, which sends the code in the form of a charge pulse sequence to the charge cradle in which the device is resting. After providing the charge pulse sequence, the system may then receive a wireless signal corresponding to a code from the device (block 168). The system then determines whether the code sent by the device is correct (block 170). In embodiments where the code sent by the device does not match the code generated by the system, the device is not paired (block 172).

Conversely, if the code sent from the device matches the code generated by the system, the system may further determine if more than one signal is present (block 174). Thus, it should be noted that there may be more than one signal indicative of a code wirelessly provided to the system, and that one, more than one, or all of the wirelessly transmitted codes may match the code generated by the system. In embodiments where more than one signal is detected (and at least one matches), the system may determine if all of the signals match (block 176). However, in embodiments where only one matching signal is detected, the device is paired (block 178).

In embodiments where only one or a portion of the signals match (i.e., not all of the signals match the generated code), then the system does not pair any of the devices (block 172), and the pairing process can be re-started or aborted. In embodiments where all of the signals match the code generated by the system, then all of the devices are paired (block 178). Further, when one or a plurality of new devices is paired, any devices that had been previously paired may be unpaired to avoid inadvertent or accidental manipulation or triggering of various system functions. For example, pairing a new handheld device with a system causes a handheld device that had been previously paired to be unpaired from the system. It should be noted that while driving, the mobile units 16 and 18 could possibly roll over bumps, causing the wireless device to bounce in its charge cradle, which could be interpreted as a pairing code. Therefore, the system could ignore or delay acting on pairing requests while the mobile drive unit is active. Additionally, the system could receive acceleration information from an accelerometer inside the system, which could indicate if the system was vibrating and therefore ignore or delay acting on a pairing request during system motion to avoid communication failures. In another embodiment, the system may define a threshold vibration value, such that in situations where the system is in motion (e.g., when driven) and experiencing vibration at or above the threshold vibration value, pairing is disabled or delayed.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray system comprising:
a source of X-ray radiation;
control circuitry configured to control the source of X-ray radiation and to communicate via a wireless interface;
a power source operatively connected to the control circuitry and capable of generating a pulse sequence corresponding to a unique pairing code generated by the control circuitry;
charge circuitry electrically connected to the power source and configured to deliver the pulse sequence as a charge sequence comprising a series of charge pulses configured to charge any one of a plurality of handheld interface devices; and
wherein the control circuitry is configured to cause the charge circuitry to deliver the pulse sequence corresponding to the unique pairing code to one of the plurality of handheld interface devices coupled to the charge circuitry, and to receive a wireless signal corresponding to the delivered code from the coupled handheld interface device to pair the coupled handheld interface device with the control circuitry.

2. The system of claim 1, wherein pairing the coupled handheld interface device with the control circuitry enables a user to control the X-ray source via the paired handheld interface device.

3. The system of claim 1, wherein pairing the coupled handheld interface device with the control circuitry enables a user to view operational parameters of the X-ray system on the paired handheld interface device.

4. The system of claim 1, further comprising a detector charge cradle electrically connected to the power source and capable of delivering the pulse sequence to any one of a plurality of wireless X-ray detectors, and wherein the control circuitry is configured to receive the generated pairing code wirelessly from the one or the plurality of wireless X-ray detectors coupled to the detector charge cradle to pair the one or the plurality of wireless X-ray detectors with the control circuitry.

5. The system of claim 4, wherein pairing the coupled one or the plurality of wireless X-ray detectors with the control circuitry enables the wireless transmission of image data from the paired wireless X-ray detectors to a remote storage system.

6. The system of claim 4, wherein pairing the one or the plurality of coupled wireless X-ray detectors with the control circuitry enables the wireless transmission of image data from the paired wireless X-ray detectors to the control circuitry.

7. The system of claim 1, comprising one or more handheld interface devices capable of receiving charge from the charge circuitry.

8. The system of claim 7, wherein the one or more handheld interface devices are configured to initiate generation of the pairing code by the control circuitry upon receiving charge from the charge circuitry, and the one or more handheld interface devices initiates generation of the pairing code by the control circuitry by wirelessly sending a pairing invitation signal.

9. The system of claim 8, wherein the one or more handheld interface devices are capable of receiving the charge sequence and wirelessly sending a signal based on the received charge sequence to the control circuitry to pair with the control circuitry.

10. The system of claim 1, wherein the code generated by the control circuitry is an 8-bit code.

11. The system of claim 1, wherein the code generated by the control circuitry is a 16-bit code.

12. The system of claim 1, wherein the X-ray system is a mobile X-ray system.

13. A method of pairing an X-ray system with a wireless device, comprising:
detecting a unique pairing code generated by a controller of the X-ray system upon receiving a pulse sequence corresponding to the unique pairing code with the device, wherein the pulse sequence comprises a series of charging pulses configured to charge the device;
transmitting a wireless signal corresponding to the unique pairing code to the controller with the device;
performing a pairing of the wireless device and the controller; and
enabling the wireless device for use with the X-ray system based upon the pairing wherein the wireless device is a component of the X-ray system.

14. The method of claim 13, comprising detecting received electrical charge from charge circuitry operatively connected to a power supply controlled by the controller and sending a wireless invitation to the controller to generate the pairing code.

15. The method of claim 14, comprising detecting the pairing code by receiving the series of charging pulses from the charge circuit, wherein the pulse sequence is generated by the power supply and the series of charging pulses comprises on/off charging cycles indicative of the pairing code.

16. The method of claim 13, wherein the device is a handheld interface device that, when enabled, enables a user to control the X-ray system wirelessly.

17. The method of claim 13, wherein the device is a wireless X-ray detector that, when enabled, allows the wireless X-ray detector to wirelessly transmit image data to the X-ray system.

18. A method of pairing an X-ray system with a wireless device, comprising:
generating a unique pairing code with control circuitry that controls the operation of the X-ray system;
providing the unique pairing code to the device in the form of a pulse sequence comprising a series of charging pulses configured to charge the device and supplied via charge circuitry operatively connected to a power supply controlled by the control circuitry;
receiving a wireless signal corresponding to the unique pairing code from the device and performing a pairing of the device with the control circuitry; and
enabling the device for use with the X-ray system wherein the wireless device is a component of the X-ray system.

19. The method of claim 18, comprising receiving a wireless invitation signal from the device to generate the unique pairing code, and wherein the unique code is generated in part or in whole from a processing clock, a MAC address, an analog sensor input, or any combination thereof, of the control circuitry of the X-ray system.

20. The method of claim 18, wherein receiving a wireless signal corresponding to the unique pairing code from the device comprises receiving a plurality of wireless signals from a plurality of devices, determining whether the wireless signals match the unique pairing code generated by the control circuitry, and enabling the plurality of devices for use with the X-ray system if the wireless signals all match, or not enabling any of the devices for use with the X-ray system if at least one of the wireless signals does not match.

21. The method of claim 18, wherein the X-ray system is a mobile X-ray system.

22. The method of claim 21, wherein pairing of the wireless device with the mobile X-ray system is disabled or delayed while the mobile X-ray system is in motion.

23. The method of claim 21, wherein pairing of the wireless device with the mobile X-ray system is either disabled or delayed while the mobile X-ray system senses vibration above a threshold value.

24. The method of claim 21, wherein the paired wireless device is configured to transmit instructions to the mobile X-ray system to drive.

25. The method of claim 18, wherein the X-ray system is a fixed room X-ray system.

26. The method of claim 25, wherein the paired wireless device is configured to control motion and positioning of the X-ray system.

27. The method of claim 18, wherein only one wireless device of a certain type is able to be paired with the X-ray system at a time.

28. The method of claim 27, wherein pairing the wireless device of a certain type with the X-ray system removes the pairing of a previously-paired wireless control device of the same type.

29. The method of claim 18, wherein when the wireless device or a second wireless device is paired and/or unpaired, wireless notifications are provided to other X-ray systems and wireless devices that the pairing and/or unpairing has occurred.

30. An imaging comprising:
a first medical device capable of wireless communication; and
a second medical device capable of wireless communication with the first medical device;
wherein the first medical device and the second medical device are configured to be dynamically paired via a charge-based pulse sequence in which the second medical device is charged via charge circuitry by a series of charge pulses corresponding to a unique paring code generated by the first medical device and delivered to the second medical device.

31. The system of claim 30, wherein the second medical device is configured to provide data to and/or receive data from the first medical device after pairing.

32. The system of claim 31, wherein the second medical device is configured to control the first medical device.

33. The system of claim 31, wherein the first medical device and the second medical device comprise an imaging system.

34. The system of claim 33, wherein the imaging system is an ultrasound imaging system.

35. The system of claim 33, wherein the imaging system is an X-ray imaging system.

* * * * *